United States Patent [19]

Ramachandran et al.

[11] Patent Number: 4,604,467

[45] Date of Patent: Aug. 5, 1986

[54] CERTAIN 4-(3,4-DIBROMOCYCLOHEXYL)PYRIDINES

[75] Inventors: Venkataraman Ramachandran; Paul F. Ranken, both of Baton Rouge, La.

[73] Assignee: Ethyl Corporation, Richmond, Va.

[21] Appl. No.: 715,672

[22] Filed: Mar. 25, 1985

Related U.S. Application Data

[62] Division of Ser. No. 511,831, Jul. 8, 1983, abandoned.

[51] Int. Cl.[4] .......................................... C07D 213/26
[52] U.S. Cl. .................................. 546/346; 546/156; 546/329
[58] Field of Search ........................................ 546/346

[56] References Cited

U.S. PATENT DOCUMENTS 4,405,792  9/1983  Walter .................................. 546/346

*Primary Examiner*—Alan L. Rotman
*Attorney, Agent, or Firm*—Donald L. Johnson; John F. Sieberth; Patricia J. Hogan

[57] ABSTRACT

A 4-cyclohexenylpyridine is brominatively aromatized to the corresponding 4-phenylpyridine by brominating the cyclohexenylpyridine, such as a 4-(halocyclohexenyl)pyridine, especially a 4-(4-halocyclohex-3-enyl)-pyridine hydrohalide, and heating the brominated product in an inert solvent and in the presence of a base to form, e.g., a 4-(halophenyl)pyridine. The invention is of particular utility in the manufacture of intermediates of antibacterial 1-alkyl-1,4-dihydro-4-oxo-7-(4-pyridyl)-3-quinolinecarboxylic acids.

3 Claims, No Drawings

CERTAIN 4-(3,4-DIBROMOCYCLOHEXYL)PYRIDINES

This application is a division of application Ser. No. 511,831, filed July 8, 1983, abandoned.

FIELD OF THE INVENTION

This invention relates to 4-phenylpyridines and a process for preparing them by the aromatization of the corresponding cyclohexenylpyridines.

BACKGROUND

U.S. Pat. No. 4,405,792, in the name of Thomas J. Walter—Walter I—discloses 4-(3-chlorocyclohex-3-enyl)pyridine, 4-(4-chlorocyclohex-3-enyl)pyridine, a process for making these compounds by a Diels-Alder reaction between chloroprene and a 4-vinylpyridine, and a process for converting them to 4-(3-chlorophenyl)pyridine and 4-(4-chlorophenyl)pyridine by catalytic dehydrogenation.

Application Ser. No. 495,977, filed May 19, 1983, in the name of Thomas J. Walter, now U.S. Pat. No. 4,533,735—Walter II—discloses processes by which 4-(4-halophenyl)pyridines, such as the 4-(4-chlorophenyl)pyridine produced in Walter I, can be converted to 4-(4-halo-3-nitrophenyl)pyridines, then to 4-(3-aminophenyl)pyridines, and ultimately to the antibacterial 1-alkyl-1,4-dihydro-4-oxo-7-pyridinyl-3-quinolinecarboxylic acids of Sterling Drug's U.S. Pat. No. 3,753,993 (Lesher et al.), U.S. Pat. No. 3,907,808 (Lesher and Carabateas), and U.S. Pat. No. 4,118,557 (Lesher).

Application Ser. No. 497,026, filed May 23, 1983, in the name of V. Ramachandran, now U.S. Pat. No. 4,533,735—Ramachandran I—discloses improved processes for preparing 4-(halocyclohex-3-enyl)pyridines and derivatives wherein a boron trifluoride catalyst is employed directly to improve the yield of 4-(halocyclohex-3-enyl)pyridine and indirectly to improve the yields of derivatives thereof.

Application Ser. No. 497,027, filed May 23, 1983, in the name of V. Ramachandran, now U.S. Pat. No. 4,550,167—Ramachandran II—discloses 4-(halocyclohex-3-enyl)pyridine salts which may be prepared by reacting 4-(halocyclohex-3-enyl)pyridines with relatively strong acids to facilitate isolating and/or aromatizing the 4-(halocyclohex-3-enyl)pyridines.

Separately and in combination, the aforementioned copending applications disclose useful processes for preparing antibacterial agents and intermediates thereof. However, since the aromatization techniques taught in these applications are not particularly efficient, there is still room for improvements in these processes. Also, it would be desirable to discover an aromatization technique that would not only permit the efficient aromatization of the difficultly aromatizable 4-(halocyclohex-3-enyl)pyridines of Walter and Ramachandran but also present an alternative method of aromatizing the more easily aromatizable 4-(cyclohex-3-enyl)pyridines having no halo substituents on the cyclohexene ring.

As described in March, *Advanced Organic Chemistry*, McGraw-Hill (New York), 1977, pages 1077–1078, it is known that cyclohexenes can be aromatized in a variety of ways in addition to the ways taught by Walter and Ramachandran. However, it is also known that these other conventional techniques are also sometimes unsatisfactory for the aromatization of particular cyclohexenes, and drastic conditions are occasionally required for the aromatization. For example, Newman et al., *Journal of the American Chemical Society*, Vol. 63, June, 1941, pages 1542–1544, disclose the inadequacy of various aromatization techniques in attempted aromatizations of 3-methyl-1,2,3,6-tetrahydrophthalic anhydride.

Newman et al. teach that their 3-methyl-1,2,3,6-tetrahydrophthalic anhydride can be aromatized by heating it with bromine in acetic acid and pyrolyzing the bromine-containing intermediate thus obtained. It would be desirable to be able to modify this brominative aromatization to make it useful for the aromatization of cyclohexenylpyridines.

SUMMARY OF INVENTION

An object of this invention is to provide a novel process for preparing 4-phenylpyridines.

Another object is to provide such a process wherein the 4-phenylpyridines are prepared from 4-cyclohexenylpyridines.

Still another object is to aromatize cyclohexenylpyridines to phenylpyridines via novel intermediates.

A further object is to provide novel processes for preparing derivatives of 4-(halophenyl)pyridines.

These and other objects are attained by brominating a 4-cyclohexenylpyridine, heating the brominated product in an inert solvent and in the presence of a base to form the corresponding 4-phenylpyridine and, when appropriate, converting the 4-phenylpyridine to a desired derivative thereof.

DETAILED DESCRIPTION

Cyclohexenylpyridines that can be used in the brominative aromatization process of the invention are cyclohexenylpyridines which are unsubstituted or bear only innocuous substituents, i.e., substituents that do not interfere with the bromination, dehydrobromination, and dehydrogenation reactions that occur in the process — such innocuous substituents including, e.g., alkyl, alkoxy, halo, carbalkoxy, cyano, etc., groups. These cyclohexenylpyridines include both compounds that are easily aromatized by known techniques and compounds which have been at least difficult to aromatize in the past.

In a particularly interesting embodiment of the invention, the cyclohexenylpyridine is a 4-(halocyclohexenyl)pyridine, which may be any 4-(halocyclohexenyl)pyridine but is generally a 4-(4-halocyclohex-3-enyl)pyridine or 4-(3-halocyclohex-3-enyl)pyridine corresponding to the formula:

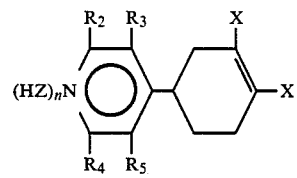

wherein HZ represents a hydrogen halide acid; n is 0 or 1; one X is halo and the other is hydrogen; and $R_2$, $R_3$, $R_4$, and $R_5$ are independently selected from hydrogen and innocuous substituents, such as substituted (e.g., halogenated) and unsubstituted alkyl, cycloalkyl, aralkyl, aryl, and alkaryl groups, optionally joined to the pyridine ring by an ether linkage; halo; cyano; carboxyl; carbalkoxy; carbamyl; nitrogen-containing heterocyclic groups, etc.—any aliphatic groups generally containing 1–6 carbons arranged in straight or branched chains.

The preferred 4-(halocyclohexenyl)pyridines are the hydrohalide salts, which are aromatized more easily than the free pyridines; and the 4-(4-chlorocyclohex-3-enyl)pyridine and 4-(3-chlorocyclohex-3-enyl)pyridine salts are especially preferred. When a product useful in preparing the aforementioned antibacterial agents is desired, the 4-(halocyclohexenyl)pyridine that is most preferred is 4-(4-chlorocyclohex-3-enyl)pyridine hydrochloride.

The 4-(halocyclohexenyl)pyridines may be prepared in any suitable manner, the preferred 4-(4-halocyclohex-3-enyl)pyridines and 4-(3-halocyclohex-3-enyl)pyridines being synthesizable, e.g., by the processes of Walter I, Ramachandran I, and Ramachandran II, the teachings of all of which are incorporated herein by reference.

The aforementioned 4-(halocyclohexenyl)pyridines are compounds which are difficult to aromatize by prior art techniques. Exemplary of the cyclohexenylpyridines which can be aromatized by known techniques but may desirably be aromatized by the process of the present invention instead of by the prior art techniques are 4-cyclohexenylpyridines, such as compounds corresponding to the formula:

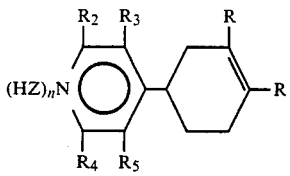

wherein HZ represents a hydrogen halide acid; n is 0 or 1; each R is independently selected from hydrogen and alkyl; and $R_2$, $R_3$, $R_4$, and $R_5$ are independently selected from hydrogen and innocuous substituents, such as substituted (e.g., halogenated) and unsubstituted alkyl, cycloalkyl, aralkyl, aryl, and alkaryl groups, optionally joined to the pyridine ring by an ether linkage; halo; cyano; carboxyl; carbalkoxy; carbamyl; nitrogen-containing heterocyclic groups, etc.—any aliphatic groups generally containing 1–6 carbons arranged in straight or branched chains. Such compounds include, e.g., 4-(cyclohex-3-enyl)pyridine, 4-(4-alkylcyclohex-3-enyl)pyridines such as 4-(4-methylcyclohex-3-enyl)pyridine, 4-(3-methylcyclohex-3-enyl)pyridine, 4-(3,4-dimethylcyclohex-3-enyl)pyridine, etc., and are typically prepared by reacting a suitable diene, such as butadiene, isoprene, etc., with an appropriate dienophile, such as a substituted or unsubstituted 4-vinylpyridine, under conditions known to the art.

In the practice of the invention, the cyclohexenylpyridine is brominated in any convenient manner, suitably by reacting one molar proportion of the cyclohexenylpyridine with at least one molar proportion of bromine in an appropriate medium, such as acetic acid, chloroform, methylene chloride, etc.—at a temperature of about 20°–70° C., for example—preferably under reflux conditions. The cyclohexenylpyridine that is brominated may be a substantially pure compound; or it may be a crude compound, such as the mixture of isomers that normally results from the Diels-Alder reactions of Walter I and Ramachandran I and II.

As indicated above, the bromination of the cyclohexenylpyridine sometimes leads to the formation of novel intermediates. For example, the bromination of a compound corresponding to the 4-(halocyclohexenyl)pyridine formula given above leads to the formation of a 4-(trihalocyclohexyl)pyridine corresponding to the formula:

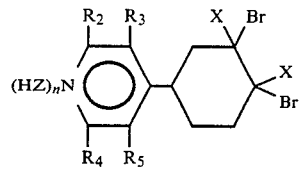

Likewise, the bromination of a compound corresponding to the 4-cyclohexenylpyridine formula given above leads to the formation of a 4-(dihalocyclohexyl)pyridine corresponding to the formula:

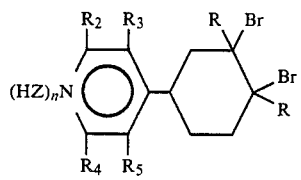

Such compounds may be generally described as 4-(3,4-dibromocyclohexyl)pyridines and include, e.g., 4-(3,4-dibromocyclohexyl)pyridine itself, 4-(3,4-dibromo-4-chlorocyclohexyl)pyridine, 4-(3,4-dibromo-4-methylcyclohexyl)pyridine, and other compounds corresponding to the formula:

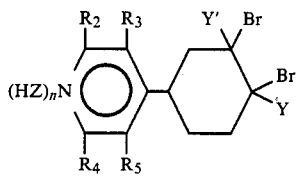

wherein Y is independently selected from hydrogen, halo, and alkyl and Y' may be hydrogen, halo, or alkyl when Y is hydrogen or alkyl and may be hydrogen or alkyl when Y is halo.

After completion of the bromination, which normally takes about 1–24 hours, e.g.—in the case of the aforementioned 4-(halocyclohexenyl)pyridines—about 12–24 hours when a free pyridine is employed and a much shorter time, e.g., about 1–3 hours, when a pyridine hydrohalide is used, the brominated product is heated to dehydrohalogenate and dehydrogenate it in a single reaction and form a phenylpyridine. This step of the process is conducted at about 80°–300° C., generally at about 100°–200° C., in an inert solvent, such as diphenyl ether, and in the presence of a base, such as potassium carbonate, sodium carbonate, sodium or potassium hydroxide, a trialkylamine, etc.

When derivatives of the phenylpyridines are to be prepared, they are generally synthesized from the phenylpyridines by conventional techniques. For example, when derivatives of the 4-(halophenyl)pyridines are desired, they may be formed by subjecting the 4-(halophenyl)pyridines to the appropriate reactions, e.g., the reactions taught in Walter II, the teachings of which are incorporated herein by reference.

When the processes of Walter II are to be used, the object is generally to form derivatives of a 4-(4-halophenyl)pyridine, which is sometimes prepared in admixture with a 4-(3-halophenyl)pyridine. In such a situation, it may be desirable first to separate the desired starting material from any isomer with which it is in admixture. However, if desired, a crude starting material, e.g., a 4-(4halophenyl)pyridine containing a 4-(3-halophenyl)pyridine impurity, may be employed in these processes.

In general, when one or more of the processes of Walter II are to be employed, a 4-(4-halophenyl)pyridine—alone or in admixture with a 4-(3-halophenyl)pyridine—is nitrated to a 4-(4-halo-3-nitrophenyl)pyridine, preferably 4-(4-chloro-3-nitrophenyl)pyridine, which may then be reduced to a 4-(3-aminophenyl)pyridine, such as 4-(3-aminophenyl)pyridine itself. Then, when antibacterial agents, such as the 1-alkyl-1,4-dihydro-4-oxo-7-pyridinyl-3-quinolinecarboxylic acids of Lesher, Lesher et al., and Lesher and Carabateas, are desired, they—or their intermediates—may be prepared by subjecting the 4-(3-aminophenyl)pyridines to suitable reactions which may be conducted by known techniques. For example:

(1) the 4-(3-aminophenyl)pyridine may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridyl)-3-quinolinecarboxylate, which in turn may be N-alkylated to an alky 1-alkyl-1,4-dihydro-4-oxo-7-(4-pyridyl)-3-quinolinecarboxylate, which may then be hydrolyzed to a 1-alkyl-1,4-dihydro-4-oxo-7-(4-pyridyl)-3-quinolinecarboxylic acid, as in Lesher et al. and Lesher and Carabateas, (2) the 4-(3-aminophenyl)pyridine may be reductively alkylated, or it may be acylated and then reduced, as in Lesher, to form a 4-(3-alkylaminophenyl)pyridine, otherwise designated as a 3-(4-pyridyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to recover a desired product for use in any other desired process, etc.

As in Walter II, when an acylated 4-(3-aminophenyl)pyridine is desired, it is sometimes convenient to combine the reduction and acylation steps, e.g., by reducing the 4-(4-halo-3-nitrophenyl)pyridine with hydrogen in the presence of sodium acetate, a palladium-on-carbon catalyst, and glacial acetic acid—a process which leads to a high yield of 4-(3-aminophenyl)pyridine at 60°-70° C. but which produces substantial yields of 4-(3-acetamidophenyl)pyridine when conducted for a sufficient time at temperatures near 80° C. Alternatively and more efficiently, 4-(3-acetamindophenyl)pyridine can be produced by including acetic anhydride in the reduction recipe.

The following example is given to illustrate the invention and is not intended as a limitation thereof.

EXAMPLE

A suitable reaction vessel was charged with 340 mg of a mixture of 70 mol % of 4-(4-chlorocyclohex-3-enyl)pyridine and 30 mol % of 4-(3-chlorocyclohex-3-enyl)pyridine, 310 mg of bromine, and 10 ml of methylene chloride and stirred at room temperature overnight. The methylene chloride was then removed by evaporation, and nmr revealed that no starting material remained in the 100 mg of product left behind.

A mixture of the crude bromination product, 340 mg of anhydrous potassium carbonate, and 10 ml of diphenyl ether was slowly heated to about 240° C. After two hours, the reaction mixture was cooled and reheated to resolubilize crystalline material.

The crude reaction mixture was taken in diethyl ether and extracted with 1N HCl, after which the acid layer was washed, neutralized, and extracted with methylene chloride to give about 400 mg of crude reaction product. Analysis of this product after drying, filtration, and evaporation showed that the reaction resulted in the production of approximately equal amounts of phenylpyridine and chlorophenylpyridine.

It is obvious that many variations may be made in the products and processes set forth above without departing from the spirit and scope of this invention.

We claim:
1. 4-(3,4-Dibromocyclohexyl)pyridine.
2. 4-(3,4-Dibromo-4-chlorocyclohexyl)pyridine.
3. 4-(3,4-Dibromo-4-methylcyclohexyl)pyridine.

* * * * *

UNITED STATES PATENT AND TRADEMARK OFFICE
CERTIFICATE OF CORRECTION

PATENT NO. : 4,604,467

DATED : August 5, 1986

INVENTOR(S) : Venkataraman Ramachandran et al.

It is certified that error appears in the above-identified patent and that said Letters Patent is hereby corrected as shown below:

Column 1, line 36, "4,533,735" should read -- 4,552,963 --;

Column 5, line 8, "4-(4halophenyl)" should read -- 4-(4-halophenyl) --;

Column 5, line 30, "alky" should read -- alkyl --.

Signed and Sealed this

Fourteenth Day of October, 1986

[SEAL]

Attest:

DONALD J. QUIGG

*Attesting Officer*   *Commissioner of Patents and Trademarks*